(12) United States Patent
Yung et al.

(10) Patent No.: US 6,453,578 B1
(45) Date of Patent: Sep. 24, 2002

(54) ORTHOPEDIC SOLE STRUCTURE

(75) Inventors: Wu-Bin Yung, Tao-Yuan; Wen-Lung Kuo, Taichung, both of (TW)

(73) Assignee: Taiwan Footwear Research Institute (TW)

(*) Notice: Subject to any disclaimer, the term of this patent is extended or adjusted under 35 U.S.C. 154(b) by 0 days.

(21) Appl. No.: 09/977,923

(22) Filed: Oct. 15, 2001

(51) Int. Cl.[7] .................. A43B 13/38; A43B 23/00; A43B 7/14; A61F 5/14
(52) U.S. Cl. ................. 36/43; 36/88; 36/166; 36/173; 36/180; 36/178; 36/181
(58) Field of Search .................. 36/43, 44, 88, 36/166, 173, 180, 91, 92, 172, 174, 176, 178, 181, 71, 148, 150, 155, 159, 160, 161

(56) References Cited

U.S. PATENT DOCUMENTS

| | | | | |
|---|---|---|---|---|
| 2,446,448 A | * | 8/1948 | Whitman | 36/178 |
| 2,902,781 A | * | 9/1959 | Rando | 36/181 |
| 2,949,685 A | * | 8/1960 | Burns | 36/178 |
| 3,470,880 A | * | 10/1969 | Pagliano | 36/178 |
| 4,112,600 A | * | 9/1978 | Hayward | 36/180 |
| 4,557,060 A | * | 12/1985 | Kawashima | 36/44 |
| 5,068,983 A | * | 12/1991 | Marc | 36/71 |
| 5,155,927 A | * | 10/1992 | Bates et al. | 36/71 |
| 5,976,100 A | * | 11/1999 | Greenawalt | 36/43 |
| 6,000,147 A | * | 12/1999 | Kellerman | 36/160 |
| 6,038,790 A | * | 3/2000 | Pyle et al. | 36/44 |
| 6,082,023 A | * | 7/2000 | Dalton | 36/43 |
| 6,176,025 B1 | * | 1/2001 | Patterson et al. | 36/44 |

FOREIGN PATENT DOCUMENTS

EP 0441068 A1 * 8/1991 ........... A43B/13/04

* cited by examiner

Primary Examiner—Anthony D. Stashick
(74) Attorney, Agent, or Firm—Webb Ziesenheim Logsdon Orkin & Hanson, P.C.

(57) ABSTRACT

An orthopedic sole structure includes an insole made from a first polymeric material with a first stiffness, and an insert made from a second polymeric material with a second stiffness. The insole includes a metatarsals support portion, a tarsals support portion and an intermediate arch support portion interposed therebetween. The intermediate arch support portion has an upper surface and a lower surface that defines a recess to receive the insert therein in such a manner that the upper surface thereof is lifted upward to permit resting of an intermediate arch portion of a user's foot when the foot is disposed on the orthopedic sole structure.

5 Claims, 7 Drawing Sheets

ORTHOPEDIC SOLE STRUCTURE

BACKGROUND OF THE INVENTION

1. Field of the Invention

The invention relates to a sole structure, more particularly to an orthopedic sole structure which is adapted to be disposed in a shoe in order to cushion a foot and which is capable of relieving foot problems.

2. Description of the Related Art

A human foot is supported by a bone structure which is made up of a metatarsals portion, a tarsals portion an intermediate arch portion interposed therebetween such that the load of the body is concentrated on the bone structure of the foot. The intermediate arch portion is substantially curved upward with respect to the metatarsals and tarsals portions, thereby forming an inwardly bent portion and consequently resulting in a void under the intermediate portion of the sole of the foot. When a foot is disposed in a shoe, most of the weight is distributed on the metatarsals and tarsals portions that rest on the sole of the shoe. In case the intermediate portion of the sole of the human foot adjacent to an inner lateral side thereof cannot form a void relative to the metatarsals and tarsals portion of the foot, discomfort and pain at the sole of the foot will be aggravated when wearing a shoe.

Figure 1:
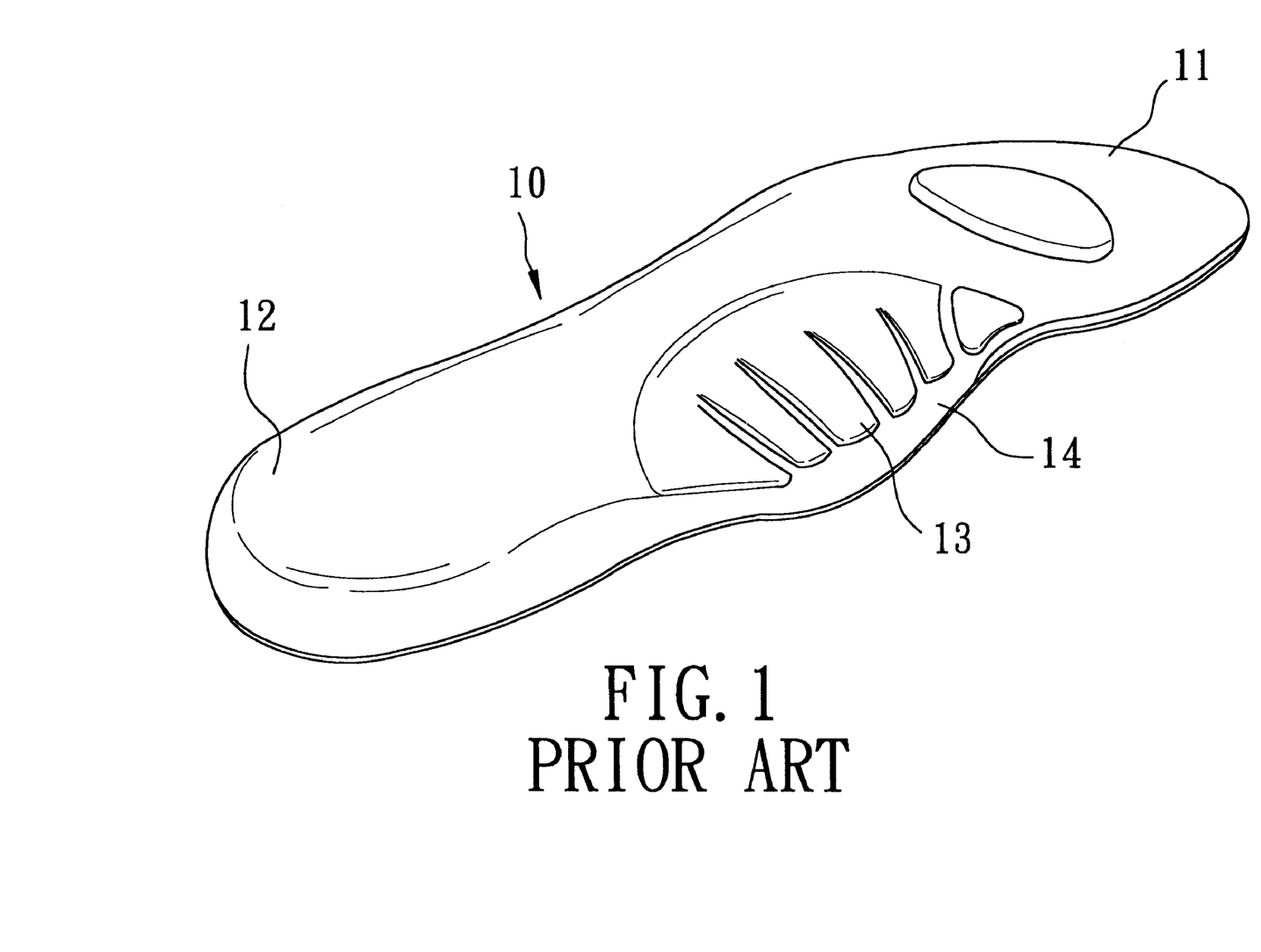
FIG. 1 is a perspective view of a conventional orthopedic sole structure.

Referring to FIG. 1, a bottom view of a conventional orthopedic sole structure for use in a shoe is shown to include an insole 10 and a cushion pad 13. The insole 10 includes a metatarsals support portion 11, a tarsals support portion 12 and an intermediate arch support portion 14 interposed therebetween. The cushion pad 13 is disposed at the intermediate arch support portion 14 of the insole 10. When a foot is disposed in a shoe provided with the aforesaid conventional orthopedic sole structure, the intermediate arch support portion 13 of the latter permits resting of the intermediate arch portion of the foot thereon, thereby relieving pain attributed to flattening of the intermediate arch portion of the foot.

It is noted that in the aforesaid conventional orthopedic sole structure, the metatarsals, tarsals and intermediate arch support portions 11,12, 14 and the cushion pad 13 are made from the same polymeric material. As such, the cushion pad 13 and the intermediate arch support portion 14 easily deform and are liable to get thinner due to weight concentration thereon and after a long period of use, thereby affecting adversely the pain relieving effect.

SUMMARY OF THE INVENTION

The object of this invention is to provide an orthopedic sole structure for use in a shoe so as to cushion the sole of a foot in order to overcome the aforesaid drawback of the prior art.

Accordingly, an orthopedic sole structure of this invention is adapted for use in a shoe to relieve pain and discomfort, and includes an insole made from a first polymeric material with a first stiffness, and an insert made from a second polymeric material with a second stiffness. The insole includes a metatarsals support portion, a tarsals support portion, and an intermediate arch support portion interposed therebetween. The insole defines an imaginary central line that extends from the metatarsals support portion toward the tarsals support portion. Each of the metatarsals and tarsals support portions has first upper and lower surfaces opposite to each other in a transverse direction relative to the central line. The intermediate arch support portion has left and right lateral edges extending between the metatarsals and tarsals support portions at opposite sides of the central line, and second upper and lower surfaces opposite to each other in the transverse direction. The second lower surface of the intermediate arch support portion has a recess which extends toward the second upper surface to terminate at a bottom, and which extends from the left lateral edge toward the right lateral edge beyond the central line, and which terminates at an abutment wall which joins with the bottom. The bottom has an inner bottom area adjacent to the abutment wall, an outer bottom area adjacent to the left lateral edge, a front bottom area adjacent to the metatarsals support portion and between the inner and outer bottom areas, and a rear bottom area adjacent to the tarsals support portion and between the inner and outer bottom areas. The insert has a configuration which complements with and which is insertable into the recess. The insert has third upper and lower surfaces opposite to each other in the transverse direction, and an inner abutment edge. The third upper surface has an inner surface area, an outer surface area, a front surface area, and a rear surface area such that when the insert is brought to be fitted in the recess to have the inner abutment edge abut against the abutment wall, the inner, outer, front and rear surface areas respectively mate with the inner, outer, front and rear bottom areas while the third lower surface of the insert is flush with the second lower surface of the intermediate arch support portion. The outer surface area is disposed at an elevation higher than the inner surface area relative to the third lower surface, thereby lifting the outer bottom area so as to permit resting of an intermediate arch portion of a user's foot thereon.

BRIEF DESCRIPTION OF THE DRAWINGS

Other features and advantages of this invention will become more apparent in the following detailed description of the preferred embodiment of this invention, with reference to the accompanying drawings, in which.

DETAILED DESCRIPTION OF THE PREFERRED EMBODIMENT

Figure 2:
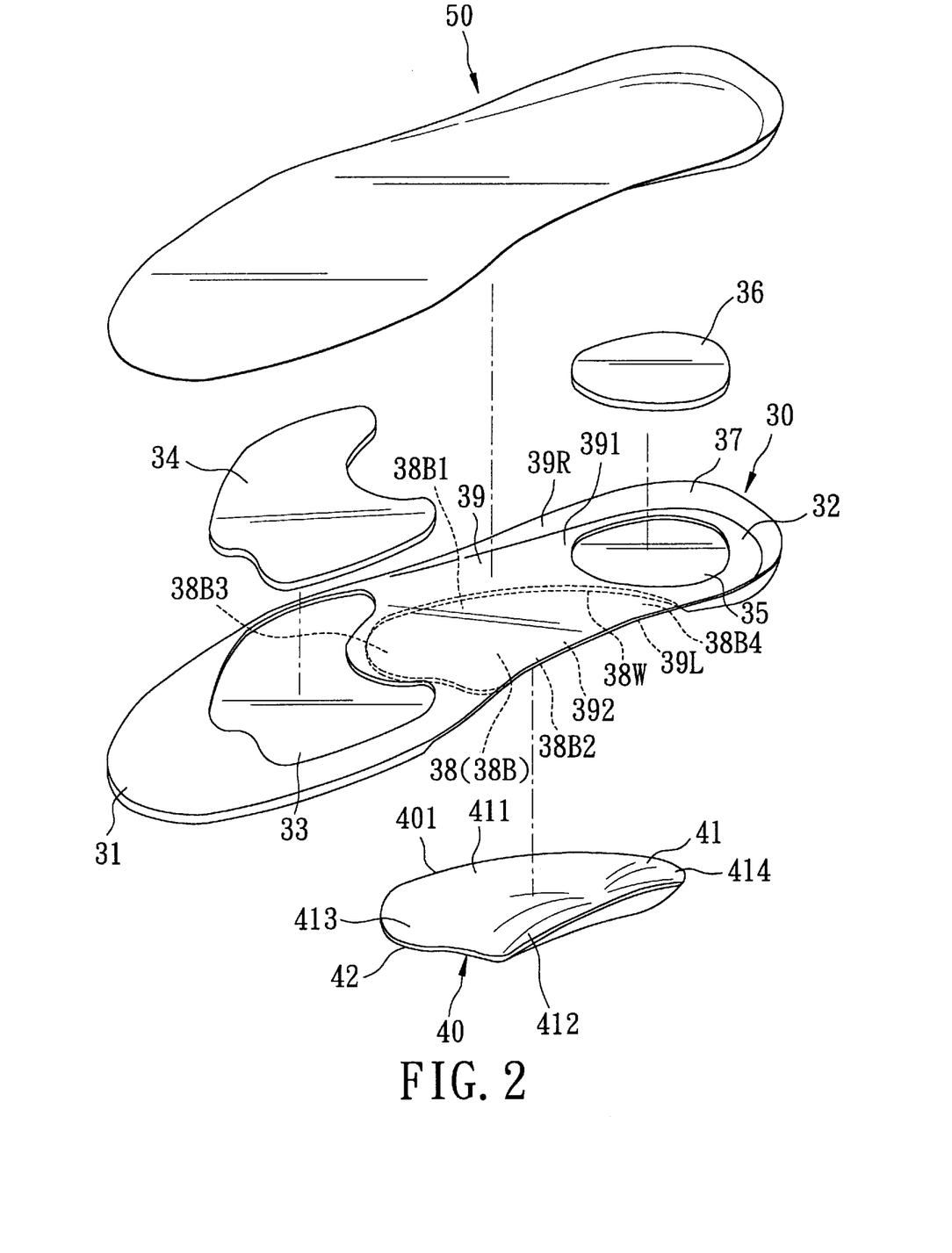
FIG. 2 is an exploded view of the preferred embodiment of an orthopedic sole structure of the present invention.
Figure 3:
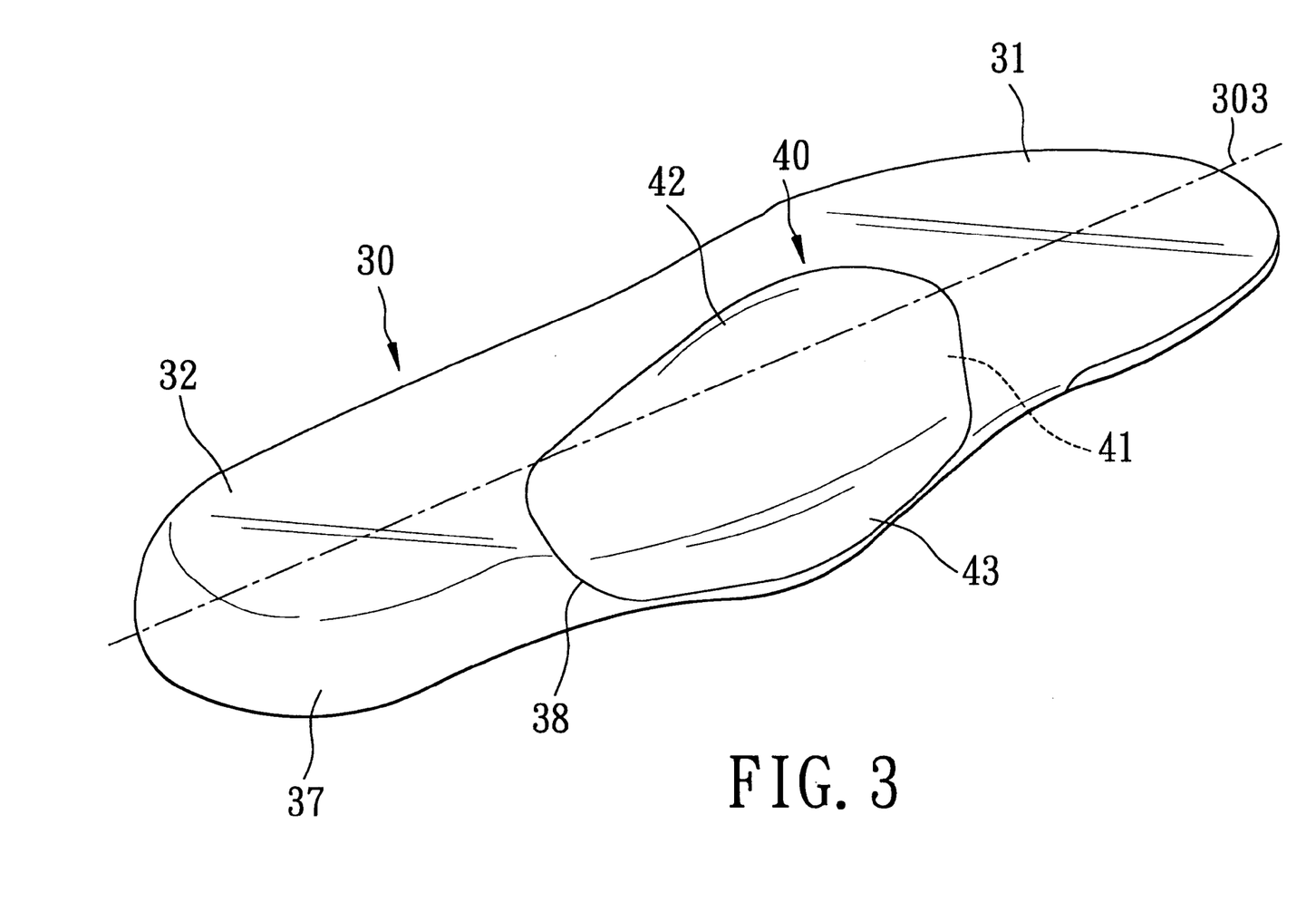
FIG. 3 is an assembled perspective view of the preferred embodiment shown in FIG. 2.
Figure 4:
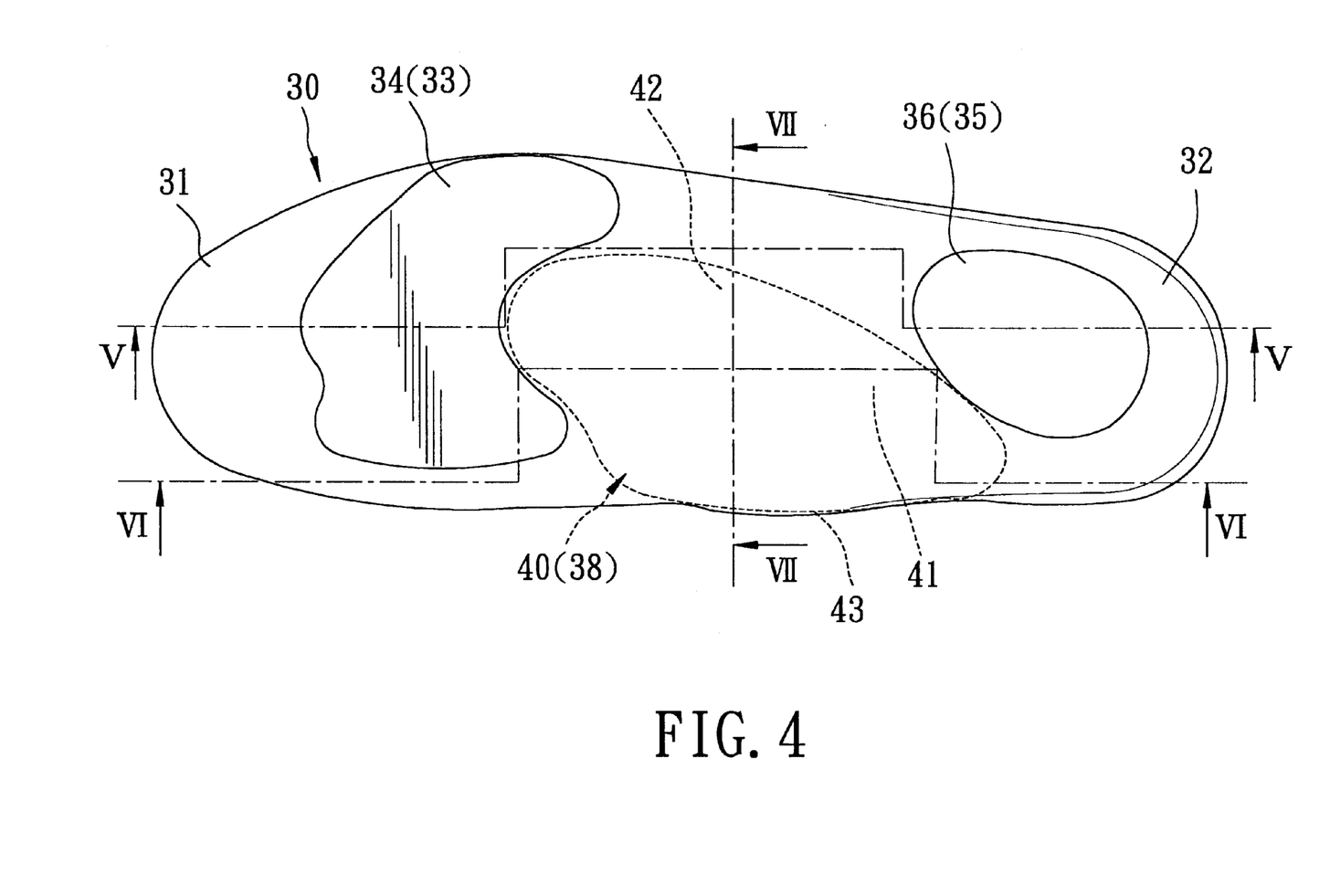
FIG. 4 is a top view of the preferred embodiment shown in FIG. 2 with an upper sole removed therefrom.

Referring to FIGS. 2, 3 and 4, the preferred embodiment of an orthopedic sole structure according to this invention is adapted for use in a shoe in order to cushion the sole of a foot of the wearer to relieve pain and discomfort, and is shown to include an insole 30 made from a first polymeric material with a first stiffness, and an insert 40 made from a second polymeric material with a second stiffness.

As illustrated, the insole 30 includes a metatarsals support portion 31, a tarsals support portion 32, and an intermediate arch support portion 39 interposed therebetween. A peripheral flange 37 extends upwardly from the periphery confining the tarsals support portion 32. The insole 30 defines an imaginary central line 303 extending from the metatarsals support portion 31 toward the tarsals support portion 32. Each of the metatarsals and tarsals support portions 31,32 has first upper and lower surfaces opposite to each other in a transverse direction relative to the central line 303. The intermediate arch support portion 39 of the insole 30 has left and right lateral edges 39L, 39R extending between the metatarsals and tarsals support portions 31,32 at opposite sides of the central line 303, and second upper and lower surfaces 391,392 opposite to each other in the transverse direction. The second lower surface 392 of the intermediate arch support portion 39 has a recess 38 which extends toward the second upper surface 391 to terminate at a bottom 38B, and which extends from the left lateral edge 39L toward the right lateral edge 39R beyond the central line 303 and which terminates at an abutment wall 38W adjoining with the bottom 38B. The bottom 38B has an inner bottom area 38B1 adjacent to the abutment wall 38W, an outer bottom area 38B2 adjacent to the left lateral edge 39L, a front bottom area 38B3 adjacent to the metatarsals support portion 31 and between the inner and outer bottom areas 38B1,38B2, and a rear bottom area 38B4 adjacent to the tarsals support portion 32 and between the inner and outer bottom areas 38B1,38B2.

Figure 6:
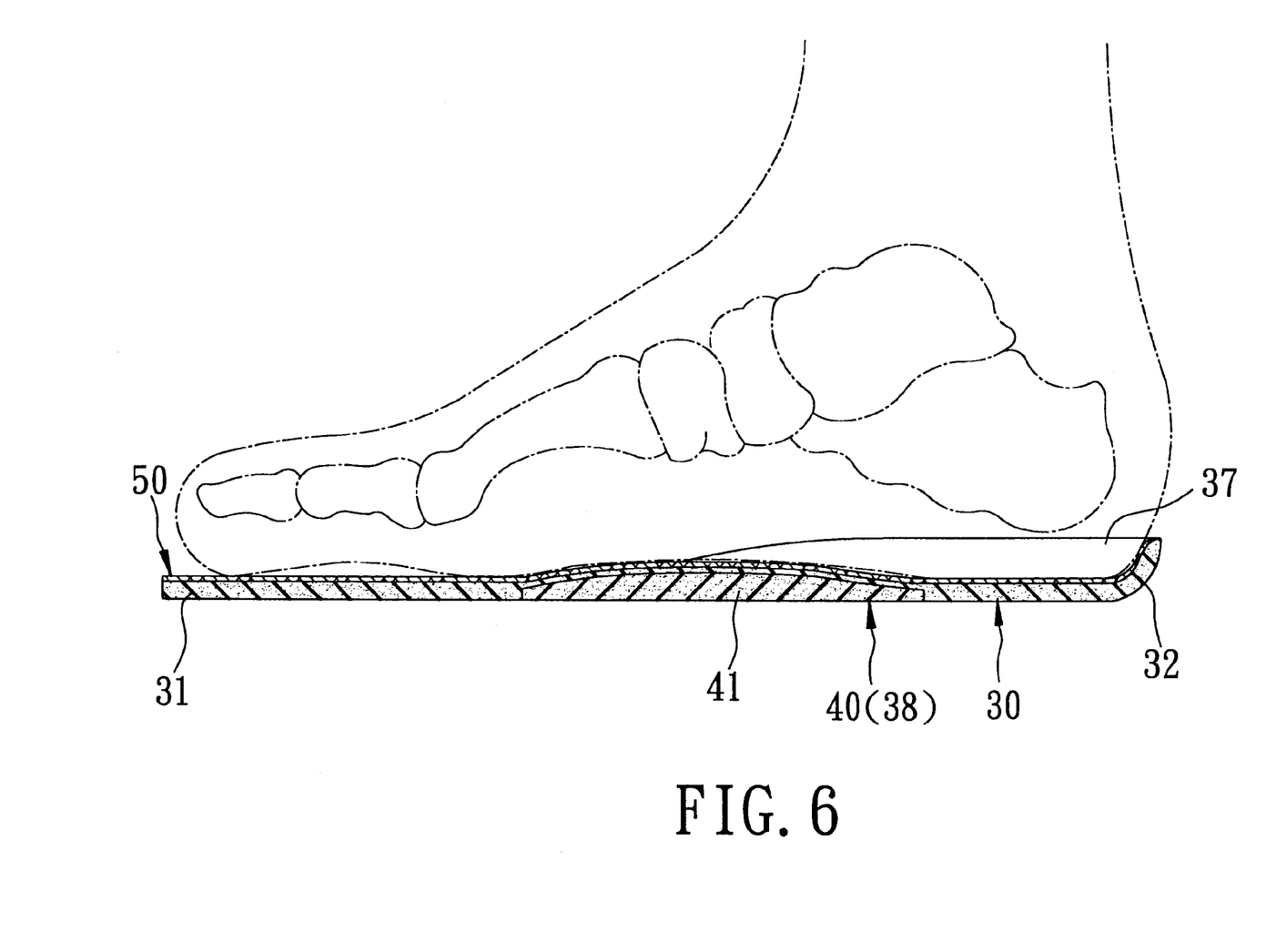
FIG. 6 is a sectional view of the preferred embodiment taken along lines VI—VI in FIG. 4.

The insert 40 is of a configuration complementing with, is insertable into the recess 38, and has third upper and lower surfaces 41,42 opposite to each other in the transverse direction, and an inner abutment edge 401. The third upper surface 41 has an inner surface area 411, an outer surface area 412, a front surface area 413, and a rear surface area 414 such that when the insert 40 is brought to be fitted in the recess 38 to have the inner abutment edge 401 abut against the abutment wall 38W, the inner, outer, front and rear surface areas 411,412,413,414 respectively mate with the inner, outer, front and rear bottom areas 38B1,38B2, 38B3, 38B4 while the third lower surface 42 of the insert 40 is flush with the second lower surface 392 of the intermediate arch support portion 39. Under this condition, the outer surface area 412 is disposed at an elevation higher than the inner surface area 411 relative to the third lower surface 42, thereby lifting the outer bottom area 38B2 so as to permit resting of an intermediate arch portion of a user's foot thereon, as best shown in FIGS. 6 and 7.

Figure 7:
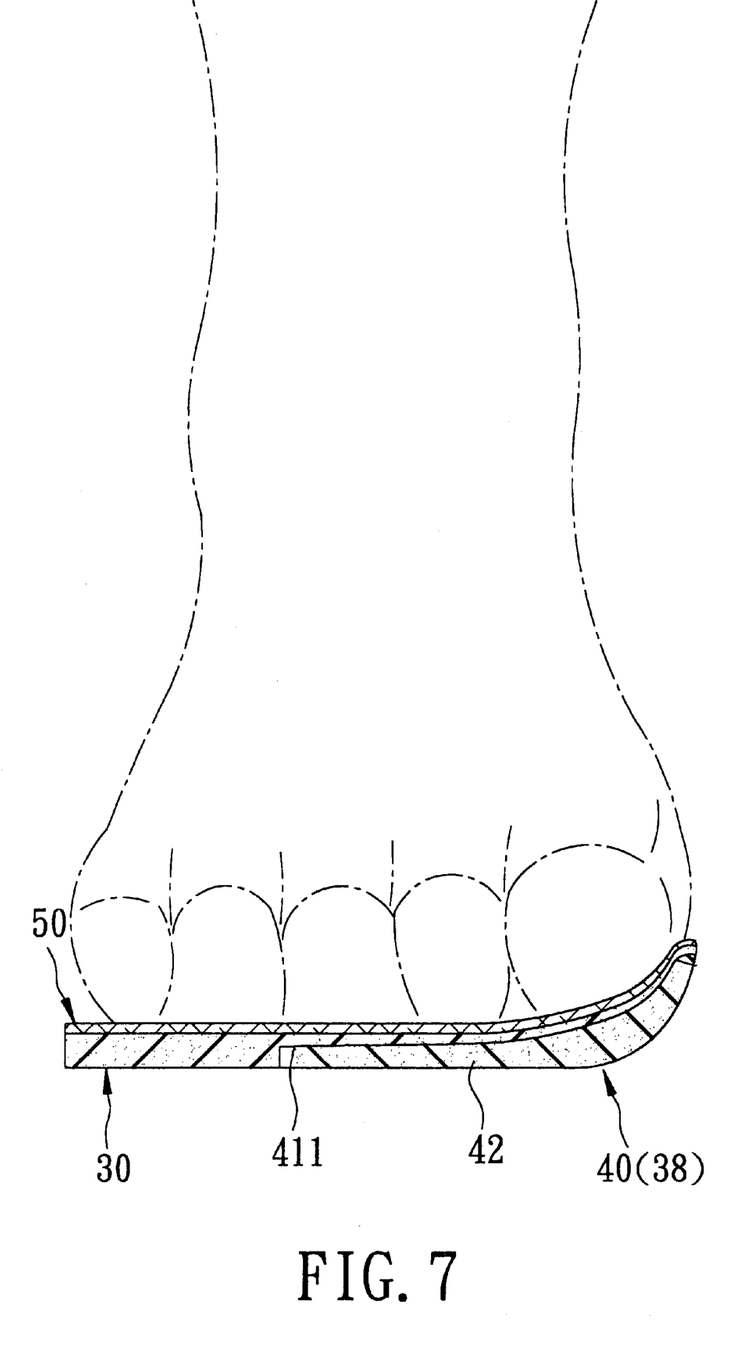
FIG. 7 is a sectional view of the preferred embodiment taken along lines VII—VII in FIG. 4.

Preferably, the outer surface area 412 of the third upper surface 41 of the insert 40 inclines gradually and downwardly toward the inner surface area 411 (see FIG. 7). Furthermore, the outer surface area 412 of the third upper surface 41 of the insert 40 inclines gradually and downwardly toward the front and rear surface areas 413,414 (see FIG. 3).

The insole 30 further has an upwardly opening front cavity 33 formed in the first upper surface of the metatarsal support portion 31, and an upwardly opening rear cavity 35 formed in the first upper surface of the tarsals support portion 32. Front and rear shock-absorbing pads 34,36 are made from a third polymeric material with a third stiffness, and have configurations and dimensions conforming with and are disposed in the front and rear cavities 33,35 respectively such that the front and rear shock-absorbing pads 34,36 cooperate with the metatarsal support portion 31 and the tarsals support portion 32 to permit resting of metatarsals and tarsals portions of the user's foot thereon, as shown in FIG. 5.

Figure 5:
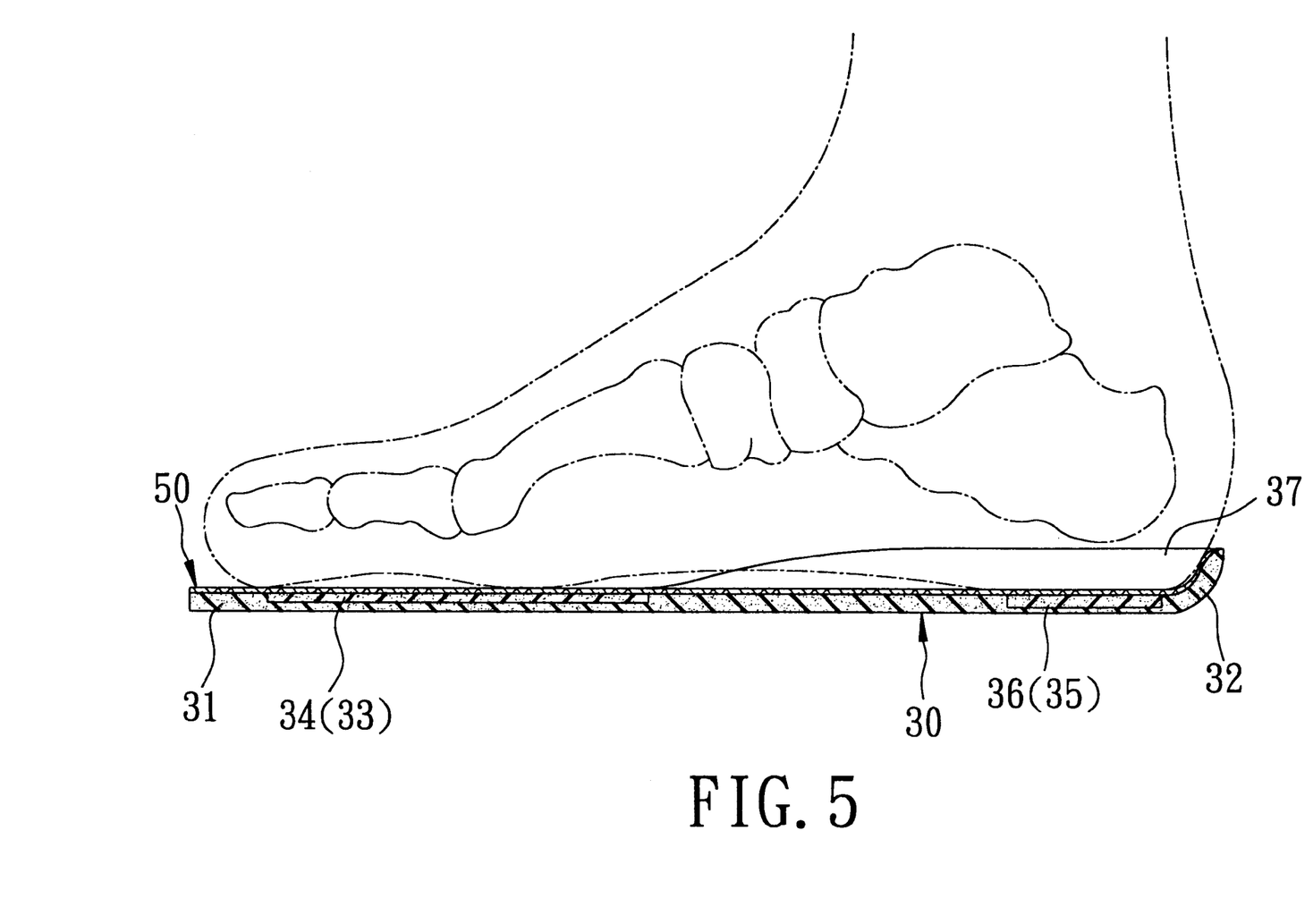
FIG. 5 is a sectional view of the preferred embodiment taken along lines V—V in FIG. 4.

An upper sole 50 is made from a fabric material with a fourth stiffness which is smaller than the first, second and third stiffness, and is superimposed upon and bonded to each of the metatarsal support portion 31, the tarsals support portion 32 and the intermediate arch support portion 39, thereby sandwiching the front and rear shock-absorbing pads 34,36 between the insole 30 and the upper sole 50, as best shown in FIG. 5.

Preferably, the first and second shock-absorbing pads 34,36 respectively project beyond the first upper surfaces of the metatarsal support portion 31 and the tarsals support portion 32.

When a human is foot is disposed in a shoe provided with an orthopedic sole structure of the present invention, the metatarsal portion and the tarsals portion of the bone structure of the foot are supported by the first and second shock-absorbing pads 34,36 (see FIG. 5), whereas the second upper surface 391 of the intermediate arch support portion 39 provides a propping action against the intermediate arch portion of the foot, as best shown in FIGS. 3 and 6.

With this invention thus explained, it is apparent that numerous modifications and variations can be made without departing from the scope and spirit of this invention. It is therefore intended that this invention be limited only as indicated in the appended claims.

We claim:

1. An orthopedic sole structure comprising:

an insole made from a first polymeric material with a first stiffness, and including a metatarsals support portion, a tarsals support portion, and an intermediate arch support portion interposed therebetween, said insole defining an imaginary central line extending from said metatarsals support portion toward said tarsals support portion, each of said metatarsals and tarsals support portions having first upper and lower surfaces opposite to each other in a transverse direction relative to said central line, said intermediate arch support portion having left and right lateral edges extending between said metatarsals and tarsals support portions at opposite sides of said central line, and second upper and lower surfaces opposite to each other in said transverse direction, said second lower surface of said intermediate arch support portion having a recess which extends inwardly toward said second upper surface to terminate at a bottom, and which extends from said left lateral edge toward said right lateral edge beyond said central line and which terminates at an abutment wall adjoining with said bottom, said bottom having an inner bottom area adjacent to said abutment wall, an outer bottom area adjacent to said left lateral edge, a front bottom area adjacent to said metatarsals support portion and between said inner and outer bottom areas, and a rear bottom area adjacent to said tarsals support portion and between said inner and outer bottom areas; and an insert made from a second polymeric material with a second stiffness and of a configuration complementing with and insertable into said recess, said insert having third upper and lower surfaces opposite to each other in said transverse direction, and an inner abutment edge, said third upper surface having an inner surface area, an outer surface area, a front surface area, and a rear surface area such that when said insert is brought to be fitted in said recess to have said inner abutment edge abut against said abutment wall, said inner, outer, front and rear surface areas respectively mate with said inner, outer, front and rear bottom areas while said third lower surface of said insert is flush with said second lower surface of said intermediate arch support portion, said outer surface area being further disposed at an elevation higher than said inner surface area relative to said third lower surface, thereby lifting said outer bottom area so as to permit resting of an intermediate arch portion of a user's foot thereon.

2. The orthopedic sole structure as defined in claim 1, wherein said outer surface area of said third upper surface of said insert inclines gradually and downwardly toward said inner surface area.

3. The orthopedic sole structure as defined in claim 2, wherein said outer surface area of said third upper surface of said insert further inclines gradually and downwardly toward said front and rear surface areas.

4. The orthopedic sole structure as defined in claim 1, wherein said insole further has an upwardly opening front cavity formed in said first upper surface of said metatarsal support portion, and an upwardly opening rear cavity formed in said first upper surface of said tarsals support portion, said sole structure further including front and rear shock-absorbing pads made from a third polymeric material with a third stiffness, said front and rear shock-absorbing pads having configurations and dimensions conforming with and being disposed in said front and rear cavities respectively such that said front and rear shock-absorbing pads cooperate with said metatarsal support portion and said tarsals support portion to permit resting of metatarsals and tarsals portions of the user's foot thereon.

5. The orthopedic sole structure as defined in claim 4, further comprising an upper sole made from a fabric material with a fourth stiffness and superimposed upon and bonded to each of said metatarsal support portion, said tarsals support portion and said intermediate arch support portion.

* * * * *